(12) United States Patent
Chollet et al.

(10) Patent No.: US 9,480,662 B1
(45) Date of Patent: Nov. 1, 2016

(54) COMPOSITIONS AND METHODS FOR TOPICAL TAMOXIFEN CITRATE THERAPY

(71) Applicants: Janet A. Chollet, Newton Center, MA (US); Fred H. Mermelstein, West Newton, MA (US)

(72) Inventors: Janet A. Chollet, Newton Center, MA (US); Fred H. Mermelstein, West Newton, MA (US)

( * ) Notice: Subject to any disclaimer, the term of this patent is extended or adjusted under 35 U.S.C. 154(b) by 0 days.

(21) Appl. No.: 14/701,960

(22) Filed: May 1, 2015

(51) Int. Cl.
*A61K 31/138* (2006.01)
*A61K 9/00* (2006.01)

(52) U.S. Cl.
CPC ........... *A61K 31/138* (2013.01); *A61K 9/0014* (2013.01); *A61K 9/0034* (2013.01)

(58) Field of Classification Search
None
See application file for complete search history.

(56) References Cited

U.S. PATENT DOCUMENTS

| | | | | |
|---|---|---|---|---|
| 2008/0026035 A1* | 1/2008 | Chollet | ................ | A61K 9/0034 424/433 |
| 2009/0092656 A1* | 4/2009 | Klamerus | ............ | A61K 9/0034 424/433 |
| 2014/0220155 A1* | 8/2014 | Takacs | ...................... | A61F 6/08 424/641 |

* cited by examiner

*Primary Examiner* — Brian J Davis
(74) *Attorney, Agent, or Firm* — Marianne Fuierer; Moore & Van Allen, PLLC

(57) ABSTRACT

The present invention provides topical compositions and methods for administering tamoxifen citrate while minimizing the incidence and or severity of adverse drug experiences associated with tamoxifen therapy. In one aspect, these compositions and methods provide a lower plasma concentration of tamoxifen metabolites, such as 4-hydroxytamoxifen and N-desmethyltamoxifen, which is presumed to be contributing at least in part to some of the adverse drug experiences, while maintaining sufficient tamoxifen as the sole active agent to benefit a subject with tamoxifen therapy.

8 Claims, 5 Drawing Sheets

Individual Vaginal Irritation Scores: Erythema - FEMALE

| Group, Animal Number | Study Interval (Day) | | | | | | | | | | | | | | | | | | | | | | | | | | | | |
|---|---|---|---|---|---|---|---|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 |
| Vehicle Control | | | | | | | | | | | | | | | | | | | | | | | | | | | | | |
| 101 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| 102 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| 103 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| 104 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| 105 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 1 |
| 106 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 1 |
| Placebo Control | | | | | | | | | | | | | | | | | | | | | | | | | | | | | |
| 107 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| 108 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| 109 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| 110 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| 111 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| 112 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Low Dose Tamoxifen | | | | | | | | | | | | | | | | | | | | | | | | | | | | | |
| 113 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| 114 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| 115 | 0 | 0 | 1 | 1 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 1 |
| 116 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| 117 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| 118 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | NDC |
| High Dose Tamoxifen | | | | | | | | | | | | | | | | | | | | | | | | | | | | | |
| 119 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| 120 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| 121 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| 122 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| 123 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| 124 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

Figure 1

Individual Recovery Vaginal Irritation Scores: Erythema - FEMALE

| Group, Animal Number | Study Interval (Day) | | | | | | | | | | | | |
|---|---|---|---|---|---|---|---|---|---|---|---|---|---|
| | 30 | 31 | 32 | 33 | 34 | 35 | 36 | 37 | 38 | 39 | 40 | 41 | 42 |
| Vehicle Control | | | | | | | | | | | | | |
| 105 | 0 | 0 | 0 | 0 | 0 | 0 | 0 | 0 | 0 | 0 | 0 | 0 | 0 |
| 106 | 0 | 0 | 0 | 0 | 0 | 0 | 0 | 0 | 0 | 0 | 0 | 0 | 0 |
| Placebo Control | | | | | | | | | | | | | |
| 111 | 0 | 0 | 0 | 0 | 0 | 0 | 0 | 0 | 0 | 0 | 0 | 0 | 0 |
| 112 | 0 | 0 | 0 | 0 | 0 | 0 | 0 | 0 | 0 | 0 | 0 | 0 | 0 |
| Low Dose Tamoxifen | | | | | | | | | | | | | |
| 116 | 0 | 0 | 0 | 0 | 0 | 0 | 0 | 0 | 0 | 0 | 0 | 0 | 0 |
| 117 | 0 | 0 | 0 | 0 | 0 | 0 | 0 | 0 | 0 | 0 | 0 | 0 | 0 |
| High Dose Tamoxifen | | | | | | | | | | | | | |
| 123 | 0 | 0 | 0 | 0 | 0 | 0 | 0 | 0 | 0 | 0 | 0 | 0 | 0 |
| 124 | 0 | 0 | 0 | 0 | 0 | 0 | 0 | 0 | 0 | 0 | 0 | 0 | 0 |

Figure 1 Cont.

Individual Vaginal Irritation Scores: Edema - FEMALE

| Group, Animal Number | Study Interval (Day) 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 |
|---|---|---|---|---|---|---|---|---|---|---|---|---|---|---|---|---|---|---|---|---|---|---|---|---|---|---|---|---|---|
| Vehicle Control | | | | | | | | | | | | | | | | | | | | | | | | | | | | | |
| 101 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| 102 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| 103 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| 104 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| 105 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 2 |
| 106 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 2 |
| Placebo Control | | | | | | | | | | | | | | | | | | | | | | | | | | | | | |
| 107 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| 108 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| 109 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| 110 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| 111 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| 112 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 1 |
| Low Dose Tamoxifen | | | | | | | | | | | | | | | | | | | | | | | | | | | | | |
| 113 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| 114 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| 115 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 2 |
| 116 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| 117 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| 118 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | NDC |
| High Dose Tamoxifen | | | | | | | | | | | | | | | | | | | | | | | | | | | | | |
| 119 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| 120 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| 121 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| 122 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| 123 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| 124 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

Figure 2

Individual Recovery Vaginal Irritation Scores: Edema - FEMALE

| Group, Animal Number | Study Interval (Day) | | | | | | | | | | | | |
|---|---|---|---|---|---|---|---|---|---|---|---|---|---|
| | 30 | 31 | 32 | 33 | 34 | 35 | 36 | 37 | 38 | 39 | 40 | 41 | 42 |
| Vehicle Control | | | | | | | | | | | | | |
| 105 | 0 | 0 | 0 | 0 | 0 | 0 | 0 | 0 | 0 | 0 | 0 | 0 | 0 |
| 106 | 0 | 0 | 0 | 0 | 0 | 0 | 0 | 0 | 0 | 0 | 0 | 0 | 0 |
| Placebo Control | | | | | | | | | | | | | |
| 111 | 0 | 0 | 0 | 0 | 0 | 0 | 0 | 0 | 0 | 0 | 0 | 0 | 0 |
| 112 | 0 | 0 | 0 | 0 | 0 | 0 | 0 | 0 | 0 | 0 | 0 | 0 | 0 |
| Low Dose Tamoxifen | | | | | | | | | | | | | |
| 116 | 0 | 0 | 0 | 0 | 0 | 0 | 0 | 0 | 0 | 0 | 0 | 0 | 0 |
| 117 | 0 | 0 | 0 | 0 | 0 | 0 | 0 | 0 | 0 | 0 | 0 | 0 | 0 |
| High Dose Tamoxifen | | | | | | | | | | | | | |
| 123 | 0 | 0 | 0 | 0 | 0 | 0 | 0 | 0 | 0 | 0 | 0 | 0 | 0 |
| 124 | 0 | 0 | 0 | 0 | 0 | 0 | 0 | 0 | 0 | 0 | 0 | 0 | 0 |

Figure 2 Cont.

COMPOSITIONS AND METHODS FOR TOPICAL TAMOXIFEN CITRATE THERAPY

FIELD OF THE INVENTION

The present invention relates to using tamoxifen citrate in a composition and delivery method that reduces plasma concentration of tamoxifen metabolites thereby reducing adverse drug effects when used for vaginal therapy to treat symptoms associated with atrophic vaginitis.

BACKGROUND OF THE INVENTION

Related Technology

Atrophic vaginitis is a hormone-dependent disease involving the lower urinary tract, genital tract, and pelvic floor. Symptoms relating to urogenital aging are due to estrogen loss and such loss accounts for the majority of the anatomical, cytological, bacteriologic, and physiologic genital changes that occur in the vagina.

With decreasing loss of estrogen, the vagina shortens, narrows, and the vaginal walls become thinner, less elastic and pale in color. As a result, numerous symptoms begin to appear. Collectively, these vaginal symptoms are referred to as atrophic vaginitis. Irritation and burning are frequently a result of a chronic discharge caused by pH elevations and bacteriologic changes of the vaginal vault. Itching, which often interferes with a restful sleep, is also due to thinning and inflammation of the vulvovaginal epithelial layer. The vaginal surface thus becomes friable, with petechiae, ulcerations, and bleeding often occurring after minimal trauma.

The most common vaginal atrophy symptom is vaginal dryness. Vaginal dryness has not only been associated with painful intercourse, but also a decrease in libido (Bachmann et al., *Maturitas* 1985; 7: 211-216). Vaginal dryness is not limited to menopausal women, in fact, women who are still menstruating also report dyspareunia and dryness.

Estrogen replacement therapy has been for many years the basis of drug therapy for the maintenance of both menopausal and non-menopausal urogenital health. However, it is well known that estrogen induces cell proliferation in mammary gland epithelium and has long been implicated as the main sex hormone in the initiation and promotion of breast cancer.

Removal of the ovaries or administration of an anti-estrogenic drug has been a major therapeutic option in breast cancer-risk patients. However, the removal of estrogen has a negative impact on a women's health, increasing the risk for osteoporosis and impeding urogenital health. For women after treatment of breast cancer, menopausal symptoms will be so severe that consideration must be given to using some form of hormonal therapy. Thus, the search for therapies, which preserve estrogen's potential benefits while avoiding undesirable estrogen effects in breast tissue, has led to the development of compounds known as selective estrogen receptor modulators (SERMs). The SERMs represent a structurally diverse group of non-steroidal compounds that can evoke either estrogen-like (agonist) or estrogen-blocking (antagonist) responses that vary by cell type and tissue.

The most successful SERM to date is tamoxifen (available commercially from Astra-Zeneca as Nolvadex®), which is a triphenylethylene derivative. It has long been thought that tamoxifen is actually a prodrug, and that its metabolites are likely to be the causative factors for the successful or negative effects seen in tamoxifen therapy. Tamoxifen metabolism mostly occurs via two pathways, 4-hydroxylation and N-demethylation, both of which result in the very potent metabolites. 4-hydroxy-tamoxifen, had been shown to be approximately 30- to 100-fold more potent as an anti-estrogen than tamoxifen (Jordon, et al. *J Endocrinol.* 1977, 75(2):305-16). However, this pathway only contributes approximately 7% of tamoxifen metabolism. N-demethylation to N-desmethyltamoxifen, catalyzed primarily by CYP3A4 and CYP3A5, contributes approximately 92% of tamoxifen metabolism (Kiyotani, et al., *Drug Metab Pharmacokinet.* 2012; 27(1):122-31). N-desmethyltamoxifen is further oxidized to a number of metabolites that appear important to tamoxifen activity, the most important being endoxifen.

Tamoxifen acts as estrogen receptor (ER) antagonists that demonstrate anti-estrogenic effects through its ability to compete with estrogen for binding sites in target tissue such as breast tissue (Fisher et al., *N Engl J Med.*, 1989; 320: 479-84). Specifically, tamoxifen is indicated for the treatment of metastatic breast cancer, for the use of adjuvant therapy for the treatment of localized breast cancer, and for the reduction of risk of breast cancer in high-risk women (Mitlak et al., *Drugs* 1999; 57: 653-663).

However, tamoxifen has been shown to act as an agonist in uterine tissue (Barakat R R, *Cancer Treat Res.* 1998; 94: 195-207). Specifically, tamoxifen stimulates uterine epithelial cell proliferation and can increase the risk of uterine cancer. Since, uterine safety is of concern to women who are considering therapy for breast cancer, the use of tamoxifen has been cautioned in non-hysterectomized patients.

There is currently only one approved method for the treatment of atrophic vaginitis, and that is the administration of exogenous estrogens. However, the FDA has imposed a warning on all FDA approved estrogens and they should not be used in subjects that are known, suspected, or history of cancer of the breast. Thus, while estrogen therapy is effective in treating atrophic vaginitis, there is poor patient compliance. Furthermore, there is no approved method for the treatment of atrophic vaginitis in breast cancer risk patients.

Notably, while the (ER) antagonist activity contributes to tamoxifen clinical usefulness, the agonist activity contributes to certain adverse complications such as increased risk of uterine cancer. More specifically, both the usefulness and adverse complications have been generally attributed to the presence and amount of active metabolites of tamoxifen, for example, 4-hydroxytamoxifen, N-desmethyltamoxifen and endoxifen.

In view of the foregoing, compositions and methods for administering tamoxifen to help minimize the incidence and/or severity of the above-described adverse effects are extremely desirable.

SUMMARY OF THE INVENTION

The present invention relates to using tamoxifen citrate in a composition and topical delivery method that reduces plasma concentration of tamoxifen metabolites thereby reducing adverse drug effects when used for vaginal therapy to treat the symptoms associated with atrophic vaginitis.

In one aspect the present invention provides for a method for minimizing an adverse drug experience associated with tamoxifen therapy, the method comprises the step of topically administering a pharmaceutical composition comprising tamoxifen citrate to a subject to provide a plasma area under the curve (AUC) ratio of a tamoxifen metabolite to tamoxifen of from about 0 to about 0.04 on day 1 and about 0.07 to about 0.14 on day 28 of dosing of an amount from about 1 mg/ml to about 20 mg/ml of tamoxifen citrate.

Specifically, the (AUC) ratio of 4-hydroxytamoxifen to tamoxifen is from about 0 to about 0.04 on day 1 and about 0.07 to about 0.14 on day 28 of dosing and the (AUC) ratio of N-desmethyltamoxifen to tamoxifen is 0 at day 1 and from about 0 to about 0.0214 at day 28 of dosing.

In another aspect, the present invention provides for a method to minimize the amount of tamoxifen metabolites, the method comprising topically applying tamoxifen citrate to vaginal tissue in a daily dosage amount of about 1 mg, wherein the formation of 4-hydroxytamoxifen is absence at day 1 and less than about 0.15 ng/ml after 28 days of dosaging.

In yet another aspect, the present invention provides for a method to minimize the amount of tamoxifen metabolites, the method comprising topically applying tamoxifen citrate to vaginal tissue in a daily dosage amount of about 1 mg, wherein the formation of N-desmethyltamoxifen is absence at day 1 and less than about 0.02 ng/ml after 28 days of dosaging.

In a still further aspect, the present invention provides a method for treating atrophic vaginitis or symptoms of atrophic vaginitis in a patient in need thereof, the method comprising:

topically administering to vaginal tissue patients suffering from atrophic vaginitis a pharmaceutical composition comprising:

a pharmaceutically effective unit dose of a sole active agent to treat atrophic vaginitis or its symptoms, wherein the sole active agent consists of tamoxifen citrate, and wherein the amount of tamoxifen citrate in the unit dose is from about 1 mg to about 20 mg; and an effective amount of a suitable carrier for vaginal administration, wherein the pharmaceutical composition provides a plasma area under the curve (AUC) ratio of a tamoxifen metabolite to a tamoxifen of from about 0 to about 0.04 on day 1 and about 0.07 to about 0.14 on day 28 of dosing of an amount from about 1 mg/ml to about 20 mg/ml, and wherein atrophic vaginitis in the patient comprises at least one symptom selected from the group consisting of a blood level measurement of Folic-Stimulating Hormone (FSH) greater than 40 mIU/ml, a vaginal pH greater than 5 and a Vaginal Maturation Index (VMI) score less than 50.

In a still further aspect the composition is prepared as a vaginal cream, gel, tablet or suppository and comprising a daily dosage of tamoxifen citrate, wherein the formation of 4-hydroxytamoxifen is absence at day 1 and less than about 0.15 ng/ml after 28 days of dosaging.

In yet another aspect, the pharmaceutical composition which comprises the tamoxifen citrate further comprises at least one constituent selected from the group consisting of additives, pharmaceutically acceptable carriers, fatty acid base, a preservative, a dye, a binder, a suspending agent, a dispersing agent, a colorant, a disintegrant, an excipient, a diluent, a lubricant, a plasticizer, oils, and mixtures thereof.

In another aspect, the present invention also provides for a method of treating symptoms of atrophic vaginitis, wherein the method includes vaginally administering an effective amount of a tamoxifen citrate to a non-hysterectomized or hysterectomized patient, wherein the sole active agent is tamoxifen and there is a reduced amount of tamoxifen metabolites, wherein the concentration in plasma of 4-hydroxytamoxifen is less than 0.36 ng/ml and the concentration of metabolite N-Desmethyltamoxifen is less than about 0.30 ng/ml after 28 days of dosage of 20 mg.

In another aspect, the present invention also provides for a method of treating symptoms of atrophic vaginitis, wherein the method includes vaginally administering an effective amount of a tamoxifen citrate to a non-hysterectomized or hysterectomized patient, wherein the sole active agent is tamoxifen and there is a reduced number of tamoxifen metabolites, wherein the plasma concentration of 4-hydroxytamoxifen is less than 0.18 ng/ml and the concentration of metabolite N-Desmethyltamoxifen is 0 after 1 day of dosage of 20 mg.

In a still further aspect of the invention, a gel or cream formulation for topical application is presented which includes a therapeutically effective amount of tamoxifen citrate which upon topical administration is sufficient to achieve a tamoxifen plasma concentration of at least about 1.3 ng/ml of plasma within about 3 hours after initiation of topical administration of about 1 mg/ml of tamoxifen citrate and with substantially no tamoxifen metabolites in plasma, as shown in FIG. 3.

In another aspect of the invention, a gel, tablet or cream formulation is provided for topical application that includes a therapeutically effective amount of tamoxifen citrate in a carrier, which upon topical administration, is sufficient to achieve a tamoxifen plasma concentration that is from about 5 to 100 times a tamoxifen metabolite plasma concentration at about 24 hours after application.

In yet another aspect, the therapeutically effective amount of tamoxifen citrate as substantially the sole active agent is effective to reduce the incidence of thrombogenic events associated with oral therapy. In a different aspect, the therapeutically effective amount of the tamoxifen citrate is effective to reduce the incidence of a worsening of climacteric symptoms and effective to reduce concomitant liability of adverse uterine effects associated with tamoxifen metabolites, such as uterine cancer.

In another aspect, the present invention provides for a method of treating symptoms of atrophic vaginitis, wherein the method includes vaginally administering an effective amount of a tamoxifen citrate to a non-hysterectomized or hysterectomized patient, wherein the sole active agent is tamoxifen and wherein the plasma of the patient is essentially free of tamoxifen metabolites. The preferable dosage amount of tamoxifen citrate is from about 0.01 to about 1.5 mg/ml and more preferably from about 0.5 to about 1 mg/ml. The term "essentially free" is meant that the plasma of the patient does not contain an amount of tamoxifen metabolites which would tend to cause adverse uterine effects associated with tamoxifen metabolites.

In a still further aspect, the tamoxifen citrate as the sole active agent with essentially no or a limited number of metabolites is topically administered for at least 3 months, preferably for at least 12 months and may be topically administered at least once a week and more preferably at least two to three times week. Alternatively the tamoxifen citrate can be topically applied daily.

These and other aspects of the invention are discussed more in the detailed description and examples.

BRIEF DESCRIPTION OF FIGURES

FIG. 1 shows the summary of vaginal irritation scores for Erythema for the 28 testing days and 14 post testing days.

FIG. 2 shows the summary of vaginal irritation scores for Edema for the 28 testing days and 14 post testing days.

DETAILED DESCRIPTION OF THE INVENTION

Figure 3:
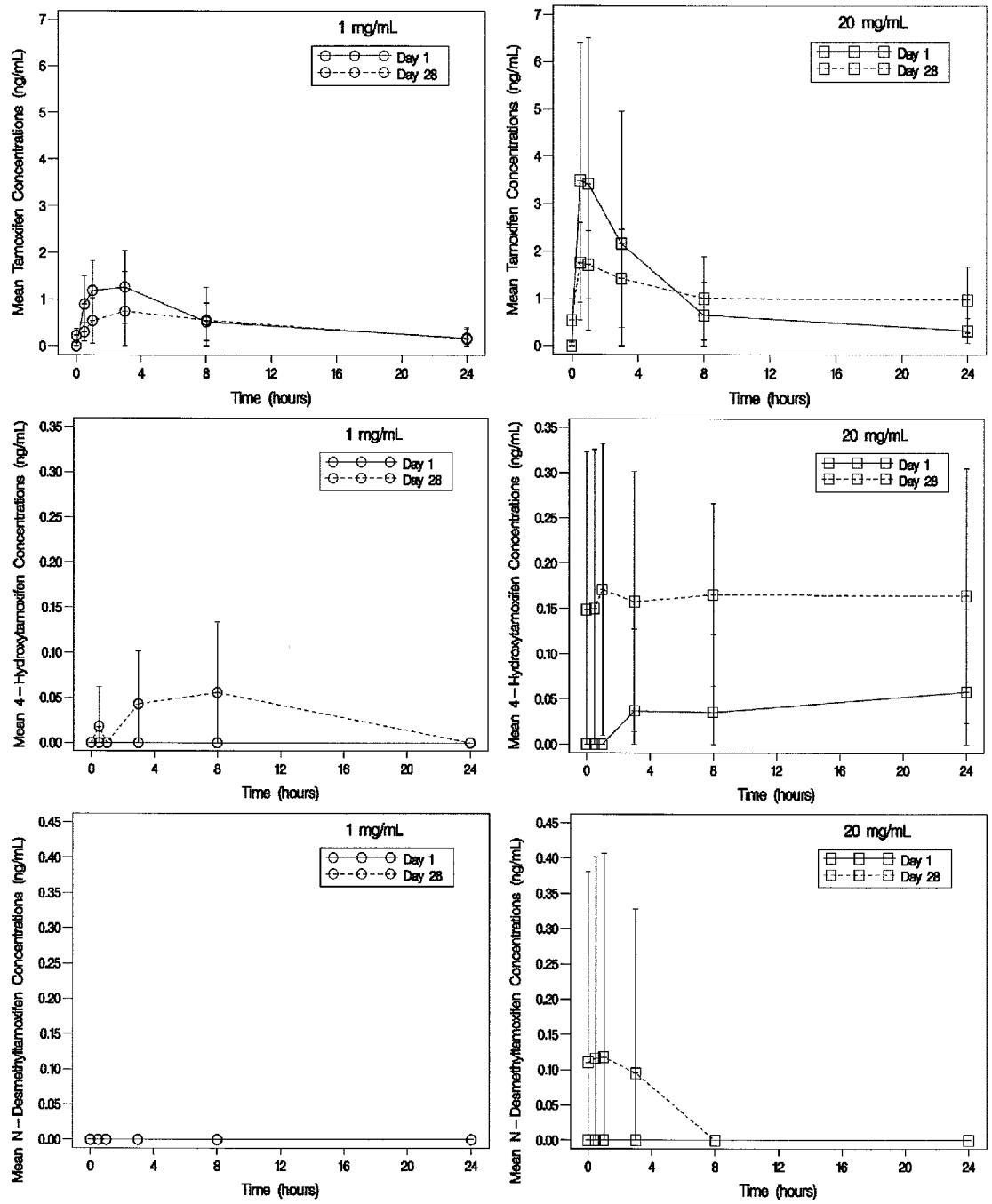
FIG. 3 shows the mean (SD) plasma Tamoxifen, 4-Hydroxytamoxifen, and N-Desmethyltamoxifen concentrations (ng/mL) on Day 1 and Day 28 following intravaginal topical administration of 1 or 20 mg/mL tamoxifen citrate as PT-101 to Female Rabbits.

The present invention advantageously provides for a method and a pharmaceutical composition for the treatment of symptoms associated with hormone deficient disorders responsive to estrogen, such as atrophic vaginitis. Moreover, the invention describes both a safe and clinically effective method to treat atrophic vaginitis. The present invention provides a long-term treatment regimen, e.g., greater than three months of continuous treatment, up to greater than 60 months of continuous treatment, while minimizing and/or inhibiting health risks associated with hormone replacement therapies. The invention is based on the discovery that tamoxifen citrate is the sole active agent when topically applied for treating atrophic vaginitis in women and not the heretofore believed metabolites.

The terms used in this specification generally have their ordinary meanings in the art, within the context of this invention and in the specific context where each term is used. Certain terms are defined below to provide additional guidance in describing the compositions and methods of the invention and how to make use of them.

DEFINITIONS

The term "estrogen receptor" refers to any protein in the nuclear receptor gene family that binds to estrogen. Human estrogen receptor in the present invention includes the alpha-receptor isoform (referred to herein as "ER-alpha") in addition to any additional isoforms as recognized by those of skill in the biochemistry arts.

The term "selective estrogen receptor modulator" (or "SERM") is a compound that exhibits activity as an agonist or antagonist of an estrogen receptor (e.g., ER-alpha) in a tissue dependent manner. Thus, as will be apparent to those of skill in the biochemistry arts, compounds of the invention that function as SERMs can act as estrogen receptor agonists in some tissues (e.g., bone, vagina, bladder and urethra) and as antagonists in other tissues types such as breast.

The terms "estrogenic effect" refer to the efficacy of a compound that exhibits agonistic activity of an estrogen receptor in a tissue dependent manner. Efficacy is measured by the induction of keratinization of the vaginal epithelium.

The terms "climacteric symptom" as used herein refers to the symptom of the climacteric which is the episodic disturbance consisting of sudden flushing and perspiration referred to as a hot flush or flash.

The terms "adverse uterine effects" refers to the stimulatory effects of estrogen on the endometrium. Adverse effects occur when the endometrium is under continuous estrogen stimulation that thus it undergoes proliferation, hyperplasia and then may progress to a histological uterine malignancy.

The term "subject" as used herein refers to a female patient in need of treatment of symptoms associated with atrophic vaginitis and may include both non-hysterectomized and hysterectomized subjects.

The term "about" or "approximately" means within an acceptable error range for the particular value as determined by one of ordinary skill in the art, which will depend in part on how the value is measured or determined, i.e., the limitations of the measurement system. For example, "about" can mean within 1 to 2 standard deviations, per the practice in the art. Alternatively, "about" can mean a range of up to 20%, and more preferably up to 5% of a given value.

The phrase "pharmaceutically acceptable" refers to molecular entities and compositions that are "generally regarded as safe" (GRAS), e.g., that are physiologically tolerable and do not typically produce an allergic or similar untoward reaction, such as gastric upset, dizziness and the like, when administered to an animal. Preferably, as used herein, the term "pharmaceutically acceptable" means approved by a regulatory agency of the Federal or state government or listed in the U.S. Pharmacopeia or other generally recognized pharmacopeia for the use in animals.

The term "carrier" refers to a diluent, adjuvant, excipient, or vehicle with which the compound is administered. Such pharmaceutical carriers can be sterile liquids, sue to its high in solubility in water, oils, including those of petroleum, animal, vegetable or synthetic origin, such as peanut oil, soybean oil, mineral oil, sesame oil and the like. Carriers such as micelles or dextran can be used to deliver the agent in an aqueous solution or suspension. E. W. Martin describes suitable pharmaceutical carriers in "Remington's Pharmaceutical Sciences".

The term "minimize" and its grammatical equivalents refer to a reduction in the frequency and or severity of one or more adverse drug experiences in a given subject or subject population.

Pharmaceutical Formulations

Tamoxifen is a selective estrogen receptor modulator. The chemical name is 1-(p-dimethylamino-ethoxphenyl)-2-ethyl-1,2-diphenylethylene. Tamoxifen has an empirical formula of $C_{26}H_{29}NO$, and has a molecular weight of 371.521. In the present invention, the preferred tamoxifen is tamoxifen citrate. The chemical name of tamoxifen citrate is (Z) 2-[4-(1,2-diphenyl-1-butenyl) phenoxy]-N, N-dimethyl-ethanamine 2-hydroxy-1,2,3-propanetricarboxylate. Tamoxifen citrate has an empirical formula of $C_{26}H_{29}NO$—$C_6H_8O_7$ and has a molecular weight of 563.62. The structure of tamoxifen citrate is shown below:

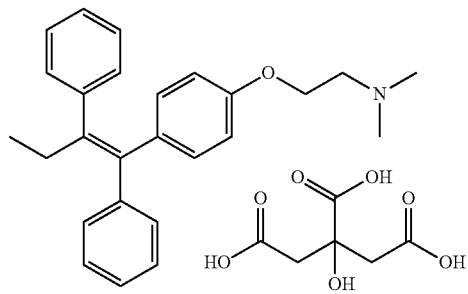

The amount of tamoxifen citrate present in the composition depends on the strength of the final composition. In one aspect, tamoxifen citrate is present in amounts ranging from about 0.01 mg per dose to about 200 mg per dose, from about 1 mg to about 30 mg per dose, from about 2 mg to about 20 mg per dose, from about 1 mg to about 5 or mg per dose and about 0.1 to 1 mg per dose. In particular suppository dosage forms, the tamoxifen citrate is present in amounts from about 1 mg to about 20 mg per dose, from about 1 mg to about 5 mg per dose or from about 0.1 to 1 mg per dose. In particular cream dosage forms, tamoxifen citrate is present in amounts from about 1 mg to about 20 mg per dose, from about 1 mg to about 5 mg per dose or from about 0.1 to about 1 mg. The dose may include from about 0.5 ml to about 4 ml of composition including the tamoxifen citrate.

Additional Constituents

The tamoxifen citrate, as the sole active agent, is formulated into a pharmaceutical composition with additional constituents for topical vaginal administration by way of suppositories, creams, foams, gels (including, but not limiting to aqueous solutions and suspensions), ointments, tablets, ovules, pessaries and rings, and other known pharmaceutically acceptable carriers known in the art.

In one embodiment of the invention, the tamoxifen citrate is formulated with a fatty base. The base may be selected from, polyethylene glycol, emollient cream, vanishing cream light, vanpen base, PEG-8 distearate, hydrogenated vitamin oil, Vitamin E Acetate and mixtures thereof.

The amount and concentrations of the constituents will correlate to an appropriate dosage form. For example, the suppository size will depend on the concentration and amount of ingredients. Preset suppository molds are contemplated in the present invention. The mold sizes range from approximately 0.5 gm to about 5.0 gm, preferably 1.28 gm, 1.4 gm, or 1.9 gm mold sizes. Cream dosages/volumes will depend on the applicator being used. The range for cream dosages may vary from about 0.5 gm to about 4.0 gm, preferably from about 0.5 gm to about 2.0 gm.

The pharmaceutical composition may include one or more additives, depending on the pharmaceutically acceptable carrier, a preservative, a dye, a binder, a suspending agent, a dispersing agent, a colorant, a disintegrate, an excipient, a diluent, a lubricant, a plasticizer, an oil or any combination of any of the foregoing. In particular embodiments, silica gel is used as a suspending agent. The amount of suspending agents will depend on the dosage and size of application, varying from about 0.01 g to about 1 gm, preferably from about 0.01 g to about 0.1 gm, preferably from about 0.01 gm to about 0.05 gm, more preferably from about 0.01 gm to about 0.03 gm. However, one skilled in the art will be able to best determine the amount of such additives. Examples of additional additives include, but are not limited to, sorbitol; talc; stearic acid; and dicalcium phosphate.

Suitable pharmaceutically acceptable additives include, but are not limited to, ethanol; water; glycerol; aloe vera gel; allantoin; glycerin; vitamin A and E oils; mineral oil; PPG2 myristyl propionate; vegetable oils and solketal.

Suitable binders include, but are not limited to starch; gelatin; natural sugars, such as glucose, sucrose and lactose; corn sweeteners; natural and synthetic gums, such as acacia, tragacanth, vegetable gum, and sodium alginate; carboxymethylcellulose; polyethylene glycol; waxes; and the like.

Suitable lubricants include, but are not limited to, sodium oleate, sodium stearate, magnesium stearate, sodium acetate, and the like.

The composition may also include suitable preservatives, e.g., sodium benzoate, and other additives that may render the composition more suitable for application, e.g., sodium chloride, which affects the osmolarity of the preparation.

Suitable dispersing and suspending agents include, but are not limited to synthetic and natural gums, such as bentoite, vegetable gum, tragacanth, acacia, alginate, dextran, sodium carboxymethylcellulose, methylcellulose, polyvinyl-pyrrolidone and gelatin.

A suitable pharmaceutical diluent is, but is not limited to, water and ethanol.

Additionally, various agents may be used to change the pH of the composition as necessary, including, for example, hydrochloric acid or sodium hydroxide, and antioxidants such as citric acid, ascorbic acid, fumaric acid and malic acid. Other possible antioxidants include palmitate, butylated hydroxyanisole, propylgallate, sodium ascorbate, and sodium metabisulfite. In particular embodiments, citric acid (0.1%) is preferably used.

In another embodiment, the tamoxifen citrate is formulated into a tablet for preferred delivery to the vaginal tissue. For example, a tablet is inserted in an applicator and delivered to the vaginal area. The tablet is designed to have adhesive ability once contacted with vaginal moisture. The tablet is designed to slowly dissolve over a number of hours. The advantages of such a delivery method over gels, creams and ointments include reduced messiness and limited leakage from the vaginal area of the active substance tamoxifen citrate.

For example, pharmaceutical preparations for tablet vaginal administration can be obtained by combining the sole active agent tamoxifen citrate ingredient with solid carriers, where appropriate granulating a resulting mixture, and processing the mixture or granulate, if desired or necessary after the addition of suitable adjuncts, into tablets or drage cores. Suitable carriers are especially fillers, such as sugars, for example, lactose, saccharose, mannitol or sorbitol, cellulose preparations and/or calcium phosphates, for example, tricalcium phosphate or calcium hydrogen phosphate, and also binders, such as starch pastes, using, for example, corn, wheat, rice or potato starch, gelatin, tragacanth, methylcellulose and/or polyvinylpyrrolidone and, if desired, disintegrators, such as the above-mentioned starches, also carboxymethyl starch, cross-linked polyvinylpyrrolidone, agar or alginic acid or a salt thereof, such as sodium alginate. Adjuncts are especially flow-regulating agents and lubricants, for example, silicic acid, talc, stearic acid or salts thereof, such as magnesium or calcium stearate, and/or polyethylene glycol. The cores may be enclosed in suitable coatings such as concentrated sugar solutions that optionally contain gum arabic, polyvinylpyrrolidone, polyethylene glycol, suitable cellulose preparations, such as acetylcellulose phthalate or hydroxypropylmethylcellulose. Coloring substances or pigments may be added to the tablets or drage coatings, for example for the purpose of identification or to indicate different doses of active ingredient.

A preferred embodiment for tablet formulation may include from about 0.1% to about 10% w/w of the sole active agent tamoxifen citrate; a diluent in an amount from about 45% to about 70% w/w wherein the diluent may include, but not limited, to lactose, starch 1500 and microcrystalline cellulose; a disintegrant in an amount of about 3% to about 8% w/w, wherein the disintegrant includes crospovidone XL; a binder in an amount from about 2% to about 10% w/w wherein the binder includes hyroxypropyl methylcellulose; and a lubricant in an amount from about 0.5% to about 2% w/w wherein the lubricant includes magnesium stearate.

Modes of Administration

Many methods may be used for vaginal administration of the formulation of the invention. These include vaginal administration of tablets in vaginal applicators, creams, suppositories, foams, gels including, but not limited to aqueous solutions and suspensions.

The pharmaceutical composition may be in a "unit dosage form", which refers to physically discrete units suitable as unitary dosages for human subjects and other mammals, each unit containing a predetermined quantity of tamoxifen citrate calculated to produce the desired therapeutic effect with substantially no tamoxifen metabolites, in association with one or more of the above-described suitable pharmaceutical diluents, excipients or carriers.

Methods of Treatment

The pharmaceutical composition of the present invention comprising tamoxifen citrate may be administered to a subject in need thereof to treat symptoms associated with atrophic vaginitis, wherein the subject may be non-hysterectomized or hysterectomized.

The invention describes both a safe and clinically effective formulation necessary to treat vaginal symptoms resulting from surgical menopause, iatrogenic menopause, natural menopause and conditions leading to suppressing estrogen levels manifesting as menopause (See Table 1).

Table 1
1. Anorexia Nervosa
2. Chromophobe Adenoma
3. Functional Hypothalamic Amenorrhea
4. Gonadal Failure
5. Gonadal Streaks
6. Gonadotrophin-Resistant Ovary Syndrome
7. Hypogonadotrophic Hypogonadism
8. Hypothalamic Dysfunction
9. Hypothalamic Failure
10. Isolated Gonadotrophin Deficiency
11. Pituitary Destruction
12. Polycystic Ovary Syndrome
13. Ovarian Destruction
14. Premature Ovarian Failure
15. Pure Gonadal Dysgenesis
16. Pituitary Failure
17. Hypothalamic etiology
18. Ovarian etiology
19. Pituitary etiology
20. Pituitary Dysfunction The pharmaceutical composition may be used to treat various conditions and symptoms of the vagina, urethra and bladder including but not limited to pain, burning, irritation itching, dryness, pressure, urinary frequency and incontinence. The compound, pharmaceutical composition, or unit dosage form of the present invention may be administered alone at appropriate dosages defined by routine testing in order to obtain greatest efficacy minimizing any potential side effects.

In other embodiments, the pharmaceutical composition can be provided in unit dosage forms containing from about 20 mg per dose of tamoxifen citrate, preferably to about 10 mg per dose, more preferably about 1 mg per dose of the tamoxifen citrate.

The present invention will be better understood by reference to the following proposed compound formulation examples, which is provided as exemplary of the invention, and not by way of limitation.

EXAMPLES

Example 1

Formulation of Triphenylethylene Derivative in Suppository Form

The present example provides a formulation of a pharmaceutical composition to treat symptoms associated with atrophic vaginitis. Table 2 summarizes the components and respective amounts of each component. JAB base is a combined formulation containing PEG-8 distearate, hydrogenated vitamin oil and Vitamin E Acetate.

TABLE 2

| | |
|---|---|
| Tamoxifen Citrate | 0.0200 gm |
| Silica Gel | 0.0150 gm |
| Base JAB: (fatty base) | 1.2485 gm |
| Suppository Volume | 1.2835 gm |
| Citric Acid 0.1% at 0.0013 gm | For pH Adjustment |

Example 2

Formulation of Triphenylethylene Derivative in Cream Form

The present example provides a formulation of a pharmaceutical composition to treat symptoms associated with atrophic vaginitis. Table 3 summarizes the components and respective amounts of each component. JC base is a combined formulation of an emollient cream and Vitamin E Acetate.

TABLE 3

| | |
|---|---|
| Tamoxifen Citrate USP | 0.0200 gm |
| Propylene Glycol USP | 0.0333 ml |
| JC Base | 0.9467 gm |
| (Base B and Base M) | |
| Base B is emollient cream | |
| Base M is Vitamin E Acetate | |
| USP Liquid (1 IU/mg) | |
| Total volume/per dose | 1.000 gm |

Example 3

A Pilot Study to Examine the Efficacy and Safety of a Tamoxifen Citrate Vaginal Suppository in Postmenopausal Hysterectomized Patients with Atrophic Vaginitis The present example presents the results of a pilot study regarding the efficacy and safety of a tamoxifen citrate vaginal suppository in postmenopausal hysterectomized patients diagnosed with atrophic vaginitis.

The primary objective of this clinical study was to evaluate the efficacy in treating atrophic vaginitis as determined by an improvement in self-assessment of vaginal dryness, and in normalization of vaginal pH. A secondary objective was to estimate the safety in treating atrophic vaginitis by serum tamoxifen metabolite concentration.

Methodology. Open-label prospective cohort study. Postmenopausal women with atrophic vaginitis were confirmed by vaginal pH. At baseline, vaginal pH and measure of her subjective vaginal dryness based on a VAS vaginal dryness. Four subjects were treated with vaginal suppositories of tamoxifen citrate for three months. After eight weeks of treatment, subjects had pharmacokinetic studies of the vaginal suppository. After three months of treatment, subjects had a vaginal pH and measure of her subjective vaginal dryness based on a VAS vaginal dryness.

Research Design. Healthy women with atrophic vaginitis were recruited to this study. To be eligible to enroll in the study, subjects underwent one screening visit. This visit was to determine the subject's vaginal pH and to measure of her subjective vaginal dryness based on a VAS. Once the subject met eligibility criteria, she received study medication.

Subjects received supplies of the study drug every six weeks. The study drug is a vaginal suppository composed of tamoxifen citrate 20 mg compounded by a local compounding pharmacist. The formulation of the text compound is provided in Table 4.

| Tamoxifen Citrate | 0.0200 gm |
|---|---|
| Silica Gel | 0.0150 gm |
| Base JAB: (fatty base) | 1.2485 gm |
| Suppository Volume | 1.2835 gm |
| Citric Acid 0.1% at 0.0013 gm | For pH Adjustment |

Subjects were instructed to insert the suppository vaginally once per day for one week and then twice per week thereafter. After eight weeks of suppository use, subjects had pharmacokinetic studies obtained. These subjects placed the suppository and remained supine for 1 hour. They then had a serum tamoxifen concentration 5 hours later. Subjects were also called once per month by the pharmacist to address any questions or concerns. At three months, subjects returned for repeat vaginal pH, and an assessment of vaginal dryness as determined by VAS.

Diagnosis and Main Criteria for Inclusion:
The study population included women of all races without a uterus.
The presence of vaginal dryness on study visit 1.
Women having follicle-stimulating hormone (FSH) levels of greater than or equal to 40mIU/ml.
A Vaginal Maturation Index of less than 50 on study visit 1.
A vaginal pH greater than 5 on study visit 1.
A normal mammogram within one year prior to study visit 1, per subject self-report.
The patient is able to use the vaginal suppository.
The following washout periods before baseline assessments were made for subjects previously on estrogen alone or estrogen/progestin containing products:
  1 week or longer for prior vaginal hormonal products (rings, creams, gels);
  4 weeks or longer for prior transdermal estrogen alone or estrogen/progestin products; 8 weeks or longer for prior oral estrogen and/or progestin therapy;
  8 weeks or longer for prior intrauterine progestin therapy;
  3 months or longer for prior progestin implants and estrogen-alone injectable drug therapy;
  6 months or longer for prior estrogen pellet therapy or progestin injectable drug therapy.

Duration of Treatment. Participants were given the vaginal suppository every day for one week and then two times per week thereafter for 3 months. They were told how to insert the test drug (using the applicator, place the study drug deep into the vagina) and the dosing schedule.

Criteria for Evaluation. The primary efficacy endpoints were normalization of vaginal pH and improvement in vaginal dryness symptom. Safety assessments consisted of monitoring and recording all adverse events and serious adverse events. The blood concentrations of tamoxifen were measured after 8 weeks of vaginal administration. The blood tests were measured after 5 hours after vaginal administration.

Statistical Methods. The primary endpoints are changes in the self-assessment of vaginal dryness and vaginal pH defined as the difference between the baseline and the 3-month measurements. Descriptive statistics provided for the continuous study endpoints will include mean, median, standard deviation, and 95% confidence intervals. Descriptive statistics provided for categorical endpoints will include frequencies, percents, and 95% confidence intervals. Missing values of a variable will be imputed using the last observed value for the participant. Descriptive statistics will be provided with and without imputation of missing values.

The secondary endpoint was the measurement of tamoxifen concentrations in plasma after 8 weeks of administration. Descriptive analysis provided for the continuous study endpoints which will also include mean.

Efficacy Results. The aim of the pilot study was to estimate the efficacy and safety of the composition in the management of postmenopausal women with atrophic vaginitis. Four subjects have completed the study. Those subjects had a mean age of 55.5 years, range 52-63, and a mean of 7.7 years post-menopause, range 2-15 years. All subjects were white. Vaginal atrophy was present in all cases at baseline.

At baseline, the median vaginal pH was 7.1, with a range of (6.5-7.5). At month 3, the median vaginal pH was 5.0 with a range of (5.0-5.2). The paired difference between baseline and month 3 had a median of −2.0, with a range of −2.5-1.5. The p-value of this paired difference, using the Wilcoxon signed rank test, was 0.07 (Table 5). This is an important finding because vaginal pH using conjugated estrogens vaginal cream given three times per week decreased to 5.2 after 4 months of treatment [Marx et al., *Maturitas* 2004; 47: 47-54]. The results are clinically meaningful because they demonstrate that tamoxifen citrate was as effective as conjugated estrogens in lowering vaginal pH after only 3 months of treatment and only administered on a twice per week regimen.

The self-assessment of vaginal dryness improved between baseline and month 3. At baseline, the median baseline vaginal dryness rating was 8.0, with a range of (7.5-9.0). At month 3, the median vaginal dryness rating was 3.0, with a range of (2.0-3.0). The paired difference between baseline and month 3 had a median of −5.5, with a range of (−6.0-4.5). The p-value of this paired difference, using the Wilcoxon signed rank test, was <0.07 (Table 5). The findings are clinically meaningful because vaginal dryness is voiced as the most bothersome problem in sexually active women who find coital activity uncomfortable because of inadequate lubrication. The finding is in agreement with other estrogen preparations demonstrating that an estrogen agonist is efficacious in the treatment of vaginal dryness resulting from vaginal atrophy [Casper et al., *Int Urogynecol J Pelvic Floor Dysfunct* 1999; 10: 171-176; Eriksen et al., *Eur J Obstet Gynecol Reprod Biol* 1992; 44: 137-14470, 71].

Median pH score and vaginal dryness symptom score, and paired differences between the enrollment and month 3 visits.

TABLE 5

| | N | Median* | Range* | P† |
|---|---|---|---|---|
| pH Enrollment | 4 | 7.1 | 6.5-7.5 | |
| pH Month 3 | 4 | 5.0 | 5.0-5.2 | |
| Paired Difference | 4 | −2.0 | −2.5--1.5 | 0.07 |
| Vaginal Dryness Enrollment | 4 | 8.0 | 7.5-9.0 | |
| Vaginal Dryness Month 3 | 4 | 3.0 | 2.0-3.0 | |
| Paired Difference | 4 | −5.5 | −6.0--4.5 | 0.07 |

*A negative value indicates a decrease from enrollment whereas a positive value indicates an increase from enrollment.
†P-value from Wilcoxon signed rank test which compared the enrollment value to the 2- and/or 12-week value for each participant.

Safety Results. All patients who received study medication received the composition completed their visits for treatment and evaluation. There were no patient drop-outs, serious adverse events, or deaths during this study. There was no reported induction or worsening of vasomotor symptoms (climacteric) such as hot flashes with treatment with the test composition. There were no reported side effects or changes to vital signs following treatment with the test composition.

In view of the long-term perspective of vaginal therapy with the test compound, tamoxifen citrate, in the treatment of urogenital atrophy, it was important to evaluate the initial pharmacokinetic profile during a maintenance therapy regimen.

Previous pharmacokinetic studies for selective estrogen receptor modulator preparations have been measured from an oral route of administration. Following a single oral dose of 20 mg tamoxifen citrate (PDR. 61 Edition. 2007: Tamoxifen: p 3527), an average peak plasma concentration of 40 ng/ml (range 35 to 45 ng/ml) occurred approximately 5 hours after dosing. The average steady state plasma concentration of tamoxifen after administration once daily for 3 months is 122 ng/ml (range 71-183 ng/ml). After initiation of therapy, steady state concentrations for tamoxifen are achieved in about 4 weeks.

In the present invention, the serum concentrations of the composition of the present invention after 8 weeks of vaginal administration were evaluated. Following a single dose of the composition, an average plasma concentration was found of 5.6 ng/ml with a range of 1.0-10.0 ng/ml, taken approximately 5 hours after dosing [Table 6]. This finding of a lower mean peak serum concentration (8-fold reduction) and a lower mean steady state serum concentration (25-fold reduction) with the test composition is clinically meaningful because it suggests that there should be less systemic side effects (deep venous thrombosis) associated with the therapy when compared to an oral route of administration.

Bioavailability of tamoxifen citrate (PT-101) after 8 weeks of Administration shown in Table 6

| Patient | Serum PT-101 (ng/ml) |
|---|---|
| 001 | 10.0 |
| 002 | 9.6 |
| 003 | 1.0 |
| 004 | 2.0 |
| Mean | 5.6 |

Conclusion. This open-label prospective cohort clinical study demonstrated that the application of the test compound in women suffering atrophic vaginitis highly efficacious in improving vaginal pH and vaginal dryness. The application of the test compound seems to produce initial pK profiles that demonstrate that the use of the test compound does not result in meaningful systemic absorption giving a reason to believe that there is little if any risk of venous thrombosis (as associated with oral therapy) associated with the use of this product candidate. In view of the increasing demand for a safe treatment for atrophic vaginitis seen in the menopause, and in keeping with reports of the excessive breast stimulation following estrogen preparations in current use, the test compound is worth special consideration since it seems to be the promising approach to a safe therapy in breast cancer risk patients. Finally, the data demonstrates that the topical vaginal application of the test compound was well tolerated and patients were generally satisfied with the product candidate as demonstrated by the low incidence of adverse events, adverse event discontinuations, ease of use and high compliance with study and medication.

Example 4

Metabolism Activity of Tamoxifen Citrate

This study was conducted to evaluate the potential local irritation effects and metabolism activity of tamoxifen citrate. The testing was conducted following once daily intravaginal administration to female rabbits for 28 days to provide evaluation of the reversibility, progression, or delayed appearance of any observed changes following a 14-day postdose observation period. The animal model most commonly used to evaluate safety of vaginally administered products is the rabbit and the ovariectomized rat. However, the rabbit is considered the more sensitive model, and thus, was selected for this study.

Assessment of toxicity and/or irritation was based on mortality, clinical observations, vaginal irritation scores, body weight, physical examinations; clinical pathology, anatomic pathology, and histopathological grading of vaginal tissues. Treatment-related microscopic findings occurred in the proximal, mid, and distal vagina.

Vehicle, Placebo, and Test Article Preparation

The vehicle, 0.9% Sodium Chloride for Injection, USP, was dispensed weekly during the study and was stored at room temperature.

The placebo was mixed with vehicle to obtain a concentration of 80 mg/ml. Fresh formulations were prepared weekly during the study and were stored at room temperature.

The test articles, 1 mg and 20 mg of tamoxifen citrate were mixed with vehicle to obtain concentrations of 1 and 20 mg/ml. Fresh formulations were prepared weekly during the study and were stored at room temperature.

Animal Acquisition and Acclimation

A total of 26 female experimentally naïve New Zealand White Hra:(NZW)SPF albino rabbits (approximately 7.5 months of age at receipt) were received from Covance Research Products, Greenfield, Ind. During the 9-day acclimation period, the animals were observed daily with respect to general health and any signs of disease.

Randomization, Assignment to Study, and Maintenance

Using a standard, by weight, measured value randomization procedure, 24 female animals (weighing 2.84 to 3.74 kg at randomization) were assigned to the control and treatment groups identified in the following Table 7.

| Group Assignments | | | |
|---|---|---|---|
| Group Number | Treatment | Tamoxifen Citrate (mg/mL) | Number of Female Animals[a] |
| 1 | Vehicle Control | 0 | 6 |
| 2 | Placebo Control | 0 | 6 |
| 3 | Low Dose Tamoxifen | 1 | 6 |
| 4 | High Dose Tamoxifen | 20 | 6 |

[a]Two animals/sex/group were maintained for a 14-day recovery period.

Animals assigned to the study had body weights within ±20% of the mean body weight. Each animal was assigned an animal number to be used in the Provantis™ data collection system and was implanted with a microchip bearing a unique identification number.

Test Article Administration

Topical vaginal administration was the route of human exposure to the test article, tamoxifen citrate. The low dose of 1 mg represents the largest potential human dose on an mg/kg basis. The high dose of 20 mg represents the largest potential total human dose unadjusted for body weight. The vehicle, 0.9% Sodium Chloride for Injection, USP, placebo, and test articles (1 mg tamoxifen citrate and 20 mg tamoxifen citrate) were administered once daily for up to 28 consecutive days during the study via intravaginal administration at a dose volume of 1 ml/animal.

The vaginal region of the animals was evaluated for signs of irritation using a modified Draize scoring system as presented in the following table. Evaluations were conducted prior to each daily dose and daily during the recovery period. Any abnormalities observed during this examination were documented as a detailed clinical observation. A score of "1" or above was confirmed by a member of the veterinary staff.

TABLE 8

Vaginal Scoring

| Score | Grade | Erythema | Edema |
|---|---|---|---|
| 0 | None | Normal color | No swelling |
| 1 | Mild | Bright pink/pale red; distinct | Defined swelling; distinct border |
| 2 | Moderate | Bright red; distinct | Defined swelling; raised border (≤1 mm) |
| 3 | Severe | Dark red/ purple; pronounced | Pronounced swelling; raised border (>1 mm) |

Vaginal irritation scores are summarized in FIGS. 1 and 2. Importantly it was found that there was no test article-related vaginal irritation evident on the study animal. Overall, low and high doses of tamoxifen citrate and the placebo control did not appear to be any more irritating than the vehicle control. Sporadic findings of mild erythema and mild to moderate edema were observed in 1 or 2 of 6 animals in the vehicle control, placebo control, and/or and low dose tamoxifen citrate groups during the 4-week dose period. This was likely the result of the dosing procedure. There were no signs of vaginal irritation during recovery period.

Plasma Analysis

Blood samples (approximately 1 mL) were collected from all testing animals via the jugular vein for determination of the plasma concentrations of the test articles and metabolites thereof. Samples were collected at predose and at 0.5, 1, 3, 8, and 24 hours postdose relative to dosing on Days 1 and 28. The animals were not fasted prior to blood collection. Samples were placed in tubes containing $K_2EDTA$ as an anticoagulant on wet ice until centrifuged. The results are shown below in Table 9 and interestingly, tamoxifen citrate was found in almost the same range as the dosing amount.

TABLE 9

Table Average Concentration Analyses (Weeks 1 to 4)

| Treatment | Nominal Tamoxifen Concentration (mg/mL) | Range of Average Calculated Concentrations (mg/mL) | Average % Recovery[a] | % RSD |
|---|---|---|---|---|
| Placebo Control | 0 | BLQ | NA | NA |
| Low Dose Tamoxifen Citrate | 1 | 0.9861-1.0177 | 98.6-101.8 | 0.137-1.557 |
| High Dose Tamoxifen Citrate | 20 | 18.8859-19.5638 | 94.4-97.8 | 0.279-0.915 |

[a]Average % recovery was calculated from the nominal concentration.
NA—Not Applicable
BLQ—Below the Limit of Quantitation Notably, it was also important to test for the plasma concentrations of the metabolites 4-Hydroxytamoxifen, and N-Desmethyltamoxifen. Summary plasma Tamoxifen, 4-Hydroxytamoxifen, and N-Desmethyltamoxifen concentration-time data on Day 1 and Day 28 following intravaginal administration of 1 or 20 mg Tamoxifen once daily to female rabbits are presented on linear-linear coordinates in FIG. 3. As such the concentrations were determined on Day 1 and Day 28 following intravaginal administration of 1 mg/mL or 20 mg/mL tamoxifen (Low Dose tamoxifen citrate and High Dose tamoxifen citrate, respectively) once daily. The mean plasma tamoxifen concentrations were observed from 0.5 to 24 hours on Day 1 and from 0 to 24 hours on Day 28 in both dose groups. Mean plasma 4-Hydroxytamoxifen concentrations were below the limit of quantitation (BLQ) at all collection times on Day 1 in the Low Dose tamoxifen citrate group and observed only at 3, 8, and 24 hours on Day 1 in the High Dose tamoxifen citrate group. On Day 28, non-BLQ mean plasma 4-Hydroxytamoxifen concentrations were observed at 0.5, 3, and 8 hours in the Low Dose tamoxifen citrate group and at all collection times in the High Dose tamoxifen citrate group. Mean plasma N-Desmethyltamoxifen concentrations were BLQ on Day 1 and Day 28 at all collection times in the Low Dose tamoxifen citrate group and on Day 28 at all collection times in the Low Dose tamoxifen citrate group. Non-BLQ mean N-Desmethyltamoxifen concentrations were observed from 0 to 3 hours on Day 28 in the High Dose tamoxifen citrate group. Specific results are shown below in Table 10:

TABLE 10

Mean (SD) Plasma Tamoxifen, 4-Hydroxytamoxifen, and N-Desmethyltamoxifen Concentrations (ng/mL) on Day 1 and Day 28 Following Intravaginal Administration of 1 or 20 mg/mL Tamoxifen as PT-101 to Female Rabbits

| Time (hours) | N | Mean Tamoxifen | SD | N | Mean 4-Hydroxytamoxifen | SD | N | Mean N-Desmethyltamoxifen | SD |
|---|---|---|---|---|---|---|---|---|---|
| Day 1 Low Dose Tamoxifen (1 | | | | | | | | | |
| 0 | 6 | 0 | 0 | 6 | 0 | 0 | 6 | 0 | 0 |
| 0.5 | 6 | 0.894 | 0.599 | 6 | 0 | 0 | 6 | 0 | 0 |
| 1 | 6 | 1.18 | 0.647 | 6 | 0 | 0 | 6 | 0 | 0 |
| 3 | 6 | 1.26 | 0.780 | 6 | 0 | 0 | 6 | 0 | 0 |
| 8 | 6 | 0.521 | 0.402 | 6 | 0 | 0 | 6 | 0 | 0 |
| 24 | 6 | 0.170 | 0.224 | 6 | 0 | 0 | 6 | 0 | 0 |
| High Dose Tamoxifen (20 | | | | | | | | | |
| 0 | 6 | 0 | 0 | 6 | 0 | 0 | 6 | 0 | 0 |
| 0.5 | 6 | 3.48 | 2.93 | 6 | 0 | 0 | 6 | 0 | 0 |
| 1 | 6 | 3.42 | 3.09 | 6 | 0 | 0 | 6 | 0 | 0 |
| 3 | 6 | 2.15 | 2.80 | 6 | 0.0368 | 0.0902 | 6 | 0 | 0 |

TABLE 10-continued

Mean (SD) Plasma Tamoxifen, 4-Hydroxytamoxifen,
and N-Desmethyltamoxifen Concentrations (ng/mL)
on Day 1 and Day 28 Following Intravaginal Administration
of 1 or 20 mg/mL Tamoxifen as PT-101 to Female Rabbits

| Time (hours) | N | Mean Tamoxifen | SD | N | Mean 4-Hydroxytamoxifen | SD | N | Mean N-Desmethyltamoxifen | SD |
|---|---|---|---|---|---|---|---|---|---|
| 8 | 6 | 0.651 | 0.697 | 6 | 0.0353 | 0.0865 | 6 | 0 | 0 |
| 24 | 6 | 0.325 | 0.261 | 6 | 0.0578 | 0.0916 | 6 | 0 | 0 |
| Day 28 Low Dose Tamoxifen (1 | | | | | | | | | |
| 0 | 6 | 0.222 | 0.153 | 6 | 0 | 0 | 6 | 0 | 0 |
| 0.5 | 6 | 0.300 | 0.195 | 6 | 0.0180 | 0.0441 | 6 | 0 | 0 |
| 1 | 6 | 0.539 | 0.480 | 6 | 0 | 0 | 6 | 0 | 0 |
| 3 | 5 | 0.744 | 0.847 | 5 | 0.0430 | 0.0590 | 5 | 0 | 0 |
| 8 | 5 | 0.557 | 0.712 | 5 | 0.0556 | 0.0787 | 5 | 0 | 0 |
| 24 | 5 | 0.154 | 0.214 | 5 | 0 | 0 | 5 | 0 | 0 |
| High Dose Tamoxifen (20 | | | | | | | | | |
| 0 | 6 | 0.538 | 0.452 | 6 | 0.149 | 0.174 | 6 | 0.111 | 0.271 |
| 0.5 | 6 | 1.76 | 0.845 | 6 | 0.150 | 0.175 | 6 | 0.117 | 0.285 |
| 1 | 6 | 1.71 | 0.719 | 6 | 0.171 | 0.161 | 6 | 0.118 | 0.289 |
| 3 | 6 | 1.42 | 1.03 | 6 | 0.158 | 0.144 | 6 | 0.0952 | 0.233 |
| 8 | 6 | 1.01 | 0.884 | 6 | 0.165 | 0.101 | 6 | 0 | 0 |
| 24 | 6 | 0.973 | 0.699 | 6 | 0.164 | 0.141 | 6 | 0 | 0 |

SD—Standard Deviation.
Source: Study files.

It can be shown from the above results that tamoxifen citrate exhibited less than dose-proportional systemic exposure on Day 1 and Day 28 over the dose range of 1 to 20 mg/ml. Little or no accumulation of tamoxifen occurred following once daily intravaginal administration of 1 and 20 mg/ml for 28 days to female rabbits. Accumulation of 4-hydroxytamoxifen could not be evaluated in the Low Dose tamoxifen group although some accumulation of 4-hydroxytamoxifen occurred in the High Dose tamoxifen group. Accumulation of N-desmethyltamoxifen could not be evaluated in either dose group. Tamoxifen accounted for approximately 85% or more of the total systemic exposure following once daily intravaginal administration of 1 to 20 mg/mL tamoxifen citrate for 28 days to female rabbits.

Pharmacokinetic Analysis

Pharmacokinetic parameters were determined by non-compartmental methods using Phoenix™ WinNonlin® (Version 6.3.0) Model: Plasma Data, Extravascular Administration for individual serial sample collection data (Pharsight Corporation). Area under the curve values were calculated using the linear trapezoidal rule with linear interpolation. Values below the limit of quantification (BLQ; i.e., <0.100 ng/mL for Tamoxifen and 4-Hydroxytamoxifen and <0.5 ng/mL for N-Desmethyltamoxifen) were treated as 0 for the analysis. Nominal sample collection time was used for the analysis unless the actual sample collection time exceeded the allowable collection window for the respective time; in which case, the actual sample collection time was used. Pharmacokinetic parameter data manipulation was performed using Excel 2010 (Microsoft Corporation).

Pharmacokinetic parameters determined were defined as follows:

$C_{max}$: Maximum observed concentration occurring at $T_{max}$. $T_{max}$: Time of maximum observed concentration.
$AUC_{0-t}$: Area under the curve from the time of dosing to the time of the last observation.

Accumulation

Exposure to Tamoxifen was generally lower on Day 28 than on Day 1 in the Low Dose Tamoxifen group (i.e., the ratio of Tamoxifen $AUC_{0-t}$ for Day 28/Day 1 was 0.672) and slightly higher on Day 28 than on Day 1 in the High Dose Tamoxifen group (i.e., the ratio of $AUC_{0-t}$ for Day 28/Day 1 was 1.15), indicating that little or no accumulation of Tamoxifen occurred following once daily intravaginal administration of 1 and 20 mg/mL Tamoxifen for 28 days to female rabbits. Accumulation of 4-Hydroxytamoxifen could not be evaluated in the Low Dose Tamoxifen group although some accumulation of 4-Hydroxytamoxifen occurred in the High Dose Tamoxifen group (i.e., the ratio of 4-Hydroxytamoxifen $AUC_{0-t}$ for Day 28/Day 1 was 4.08). Accumulation of N-Desmethyltamoxifen could not be evaluated in either dose group.

Metabolite to Parent Drug Ratios

Exposure from Tamoxifen was greater than from 4-Hydroxytamoxifen and N-Desmethyltamoxifen on both Day 1 and Day 28. Ratios of mean 4-Hydroxytamoxifen to Tamoxifen $Auc_{0-t}$ values could not be determined in the Low Dose Tamoxifen group and was 0.0419 in the High Dose Tamoxifen group on Day 1. Ratios of mean 4-Hydroxytamoxifen to Tamoxifen $AUC_{0-t}$ values ranged from 0.0702 to 0.148 on Day 28. Ratios of mean N-Desmethyltamoxifen to Tamoxifen $AUC_{0-t}$ values could only be determined in the High Dose Tamoxifen group on Day 28 (0.0214). These findings indicated that Tamoxifen accounted for approximately 85% or more of the total systemic exposure to Tamoxifen, 4-Hydroxytamoxifen, and N-Desmethyltamoxifen following once daily intravaginal administration of 1 to 20 mg/mL Tamoxifen as PT-101 for 28 days to female rabbits.

Pharmacokinetic Parameters

Summary plasma Tamoxifen, 4-Hydroxytamoxifen, and N-Desmethyltamoxifen pharmacokinetic parameters on Day 1 and Day 28 following intravaginal administration of 1 or 20 mg/mL Tamoxifen as PT-101 once daily are presented in Table 11. Median Tamoxifen $T_{max}$ ranged from 0.5 to 1 hour on Day 1 and Day 28. Mean Tamoxifen $C_{max}$ ranged from 1.44 to 3.65 ng/mL on Day 1 and from 0.824 to 2.33 ng/mL on Day 28. Mean Tamoxifen $AUC_{0-t}$ ranged from 13.2 to 23.0 ng*hr/mL on Day 1 and from 8.85 to 26.5 ng*hr/mL on Day 28. Median 4-Hydroxytamoxifen $T_{max}$ could not be determined in the Low Dose Tamoxifen group on Day 1. Median 4-Hydroxytamoxifen $T_{max}$ in the High Dose Tamoxifen group was 13.5 on Day 1 and ranged from 1 to 8 hours on Day 28. Mean 4-Hydroxytamoxifen $C_{max}$ ranged from 0 to 0.0708 ng/mL on Day 1 and from 0.0463 to 0.219 ng/mL on Day 28. Mean 4-Hydroxytamoxifen $AUC_{0-t}$ ranged from 0 to 0.963 ng*hr/mL on Day 1 and from 0.621 to 3.93 ng*hr/mL on Day 28. Median N-Desmethyltamoxifen $T_{max}$ could not be determined on Day 1 in either dose group or on Day 28 in the Low Dose Tamoxifen group; median N-Desmethyltamoxifen $T_{max}$ was 1 hour on Day 28 in the High Dose Tamoxifen group. Mean N-Desmethyltamoxifen $C_{max}$ was 0 ng/mL and $Auc_{0-t}$ was 0 ng*hr/mL in both dose groups on Day 1 and in the Low Dose Tamoxifen group on Day 28. Mean N-Desmethyltamoxifen $C_{max}$ was 0.118 ng/mL and mean $Auc_{0-t}$ was 0.566 ng*hr/mL in the High Dose Tamoxifen group on Day 28.

TABLE 11

Mean (SD) Tamoxifen, 4-Hydroxytamoxifen, and N-Desmethyltamoxifen Pharmacokinetic Parameters on Day 1 and Day 28 Following Intravaginal Administration of 1 or 20 mg/mL Tamoxifen as PT-101 to Female Rabbits

| Analyte | | Tamoxifen Dose (mg/mL) | * Tmax (hr) | Cmax (ng/mL) | AUC0-t (ng * hr/mL) | Cmax/Dose [(ng/mL)/ (mg/kg)] | AUC0-t/Dose [(ng * hr/mL)/ (mg/kg)] |
|---|---|---|---|---|---|---|---|
| | | | Day 1 | | | | |
| Mean (SD) | Tamoxifen | 1 | 1 (0.786) | 1.44 | 13.2 (8.24) | 1.44 (0.786) | 13.2 (8.24) |
| Mean (SD) | Tamoxifen | 20 | 0.5 (2.96) | 3.65 | 23.0 (23.7) | 0.182 (0.148) | 1.15 (1.19) |
| | | | Day 28 | | | | |
| Mean (SD) | Tamoxifen | 1 | 1.0 (0.819) | 0.824 | 8.85 (11.6) | 0.824 (0.819) | 8.85 (11.6) |
| Mean (SD) | Tamoxifen | 20 | 0.5 (0.667) | 2.33 | 26.5 (16.4) | 0.116 (0.0333) | 1.32 (0.820) |
| Ratio[a] | | | | | | 7.88 | 11.5 |
| Ratio[b] | | | | | | 7.08 | 6.68 |
| Ratio[c] | | | | | 0.672, 1.15 | | |
| | | | Day 1 | | | | |
| Mean (SD) | 4-Hydroxytamoxifen | 1 | . (0) | 0 | 0 (0) | 0 (0) | 0 (0) |
| Mean (SD) | 4-Hydroxytamoxifen | 20 | 13.5 (0.110) | 0.0708 | 0.963 (1.69) | 0.00354 (0.00549) | 0.0481 (0.0845) |
| | | | Day 28 | | | | |
| Mean (SD) | 4-Hydroxytamoxifen | 1 | 8 (0.0739) | 0.0463 | 0.621 (0.985) | 0.0463 (0.0739) | 0.621 (0.985) |
| Mean (SD) | 4-Hydroxytamoxifen | 20 | 1 (0.140) | 0.219 | 3.93 (2.89) | 0.0109 (0.00701) | 0.196 (0.145) |
| Ratio[a] | | | | | | ND | ND |
| Ratio[b] | | | | | | 4.24 | 3.16 |
| Ratio[c] | | | | | ND, 4.08 | | |
| Ratio[d] | | | | | ND, 0.0419 | | |
| Ratio[e] | | | | | 0.0702, 0.148 | | |
| | | | Day 1 | | | | |
| Mean (SD) | N-Desmethyltamoxifen | 1 | . (0) | 0 | 0 (0) | 0 (0) | 0 (0) |
| Mean (SD) | N-Desmethyltamoxifen | 20 | . (0) | 0 | 0 (0) | 0 (0) | 0 (0) |
| | | | Day 28 | | | | |
| Mean (SD) | N-Desmethyltamoxifen | 1 | . (0) | 0 | 0 (0) | 0 (0) | 0 (0) |
| Mean (SD) | N-Desmethyltamoxifen | 20 | 1 | 0.118 (0.289) | 0.566 (1.39) | 0.00589 (0.0144) | 0.0283 (0.0694) |
| Ratio[a] | | | | | | ND | ND |
| Ratio[b] | | | | | | ND | ND |
| Ratio[c] | | | | | ND | | |
| Ratio[f] | | | | | ND, ND | | |
| Ratio[g] | | | | | ND, 0.0214 | | |

Median $_{Tmax}$ reported.
[a]Ratio of high to low mean values on Day 1.
[b]Ratio of high to low mean values on Day 28.
[c]Ratios of mean values on Day 28 to Day 1.
[d]Ratio of mean 4-Hydroxytamoxifen to Tamoxifen values on Day 1.
[e]Ratio of mean 4-Hydroxytamoxifen to Tamoxifen values on Day 28.
[f]Ratio of mean N-Desmethyltamoxifen to Tamoxifen values on Day 1.
[g]Ratio of mean N-desmethyltamoxifen to Tamoxifen values on Day 28.
SD—Standard Deviation.
ND—Not Determined. Source: Study files.

Example 5

Formulation of tablet form of the present invention include a film-coated tablet containing 1.5 mg, 7.6 mg or 30.4 mg of tamoxifen citrate equivalent to 1 mg, 5 mg, and 20 mg tamoxifen free base respectively and a mix of inactive excipients. The components of the formulated product are provided in Table 12.

TABLE 12

Composition of 1-mg, 5-mg and 20-mg tablets

| Component | Function | Amount per unit (mg/tablet) | | |
|---|---|---|---|---|
| | | 1-mg | 5-mg | 20-mg |
| Core Tablet | | | | |
| Tamoxifen citrate | Active | 1.5 | 7.6 | 30.4 |
| Lactose | Diluent | 38.0 | 38.6 | 25.4 |
| Starch 1500 | Diluent | 16.3 | 16.6 | 10.9 |
| Microcrystalline cellulose | Diluent | 18.2 | 11.1 | 7.3 |
| Crospovidone XL | Disintegrant | 3.2 | 3.2 | 3.2 |
| Methocel E5P (Hyroxypropyl Methylcellulose) | Binder | 2.2 | 2.2 | 2.2 |
| Magnesium stearate | Lubricant | 0.6 | 0.6 | 0.6 |
| Tablet weight | | 80 | 80 | 80 |
| Film-Coating | | | | |
| Hyroxypropyl Methylcellulose | Film Former | 4.15 | 4.15 | 4.15 |
| Macrogol 4000 | Plasticizer | 0.85 | 0.85 | 0.85 |

Process of formulation includes dissolving hydroxypropyl methyl cellulose (Methocel E5P) in water as the granulating medium. Tamoxifen citrate, starch, lactose and microcrystalline cellulose, crospovidone are blended and wet granulated with the above granulation medium. The wet granulation is dried in the oven at 40° C., and then milled in a Comill. Magnesium stearate is added as the extragranular excipient. The 80-mg tablets are compressed in an 8-station tablet press with 6.0 mm round concave tooling. Tablets are spray coated with a solution containing HPMC and PEG-4000 in water.

The above results show that tamoxifen citrate is the sole active compound and the compound that is driving the efficacy mediating the biological activity for the treatment of atrophic vaginitis or symptoms of atrophic vaginitis. This is determined in light of the fact that the pharmacokinetic data unexpectedly showed little to no metabolism of the parent compound or detectable levels of the active metabolites in the plasma of the testing rabbits treated over four weeks with vaginal administration of tamoxifen citrate.

The present invention is not limited in scope by the specific embodiments described herein. Indeed, various modifications of the invention in addition to those described herein will become apparent to those in the skilled in the art from the forgoing description and the accompanying figures. Such modifications are intended to fall within the scope of the appended claims.

Patents, patent application, publications, product descriptions, and protocols are cited throughout this application, the disclosures of which are incorporated herein by reference in their entireties for all purposes.

That which is claimed is:

1. A method for reducing plasma concentration of tamoxifen metabolites associated with tamoxifen therapy, the method comprising:
   topically administering a pharmaceutical composition to a subject comprising tamoxifen citrate to a subject to provide a plasma area under the curve (AUC) ratio of a tamoxifen metabolite to tamoxifen of from about 0 to about 0.04 on day 1 and about 0.07 to about 0.14 on day 28.

2. The method of claim 1, wherein the pharmaceutical composition comprises from about 0.01 mg/ml to about 20 mg/ml of tamoxifen citrate.

3. The method of claim 1, wherein the pharmaceutical composition comprises from about 0.5 mg/ml to about 1.5 mg/ml of tamoxifen citrate.

4. The method of claim 1, wherein the pharmaceutical composition is topically administered for at least 3 months or at least 12 months.

5. The method of claim 1, wherein the pharmaceutical composition is topically administered daily, two times a week or at least three times a week.

6. A method for treating atrophic vaginitis or symptoms of atrophic vaginitis in a patient in need thereof, the method comprising:
   topically administering to vaginal tissue patients suffering from atrophic vaginitis a pharmaceutical composition comprising:
   a pharmaceutically effective unit dose of a sole active agent to treat atrophic vaginitis or its symptoms, wherein the sole active agent consists of tamoxifen citrate; and
   an effective amount of a suitable carrier for vaginal administration,
   wherein the pharmaceutical composition provides a plasma area under the curve (AUC) ratio of a tamoxifen metabolite to a tamoxifen of from about 0 to about 0.04 on day 1 and about 0.07 to about 0.14 on day 28 by topically administering the pharmaceutical composition on a daily basis with a concentration from about 1 mg/ml to about 20 mg/ml, and wherein atrophic vaginitis in the patient comprises at least one symptom selected from the group consisting of a blood level measurement of Folic-Stimulating Hormone (FSH) greater than 40 mIU/ml, a vaginal pH greater than 5 and a Vaginal Maturation Index (VMI) score less than 50.

7. The method of claim 6, wherein the (AUC) ratio of 4-hydroxytamoxifen to tamoxifen is from about 0 to about 0.04 on day 1 and about 0.07 to about 0.14 on day 28 of dosing.

8. The method of claim 6, wherein the pharmaceutical composition further comprises at least one constituent selected from the group consisting of additives, pharmaceutically acceptable carriers, fatty acid base, a preservative, a dye, a binder, a suspending agent, a dispersing agent, a colorant, a disintegrant, an excipient, a diluent, a lubricant, a plasticizer, oils, and mixtures thereof.

* * * * *